US008546103B2

(12) United States Patent
Edberg

(10) Patent No.: US 8,546,103 B2
(45) Date of Patent: *Oct. 1, 2013

(54) **METHOD FOR DETECTING THE PRESENCE OR ABSENCE OF PATHOGENIC *STAPHYLOCOCCI* IN A TEST SAMPLE, INCLUDING TEST MIXTURE WITH MICRO PARTICLES**

(75) Inventor: Stephen C. Edberg, Longboat Key, FL (US)

(73) Assignee: Pilots Point, LLC, Sarasota, FL (US)

( * ) Notice: Subject to any disclaimer, the term of this patent is extended or adjusted under 35 U.S.C. 154(b) by 331 days.

This patent is subject to a terminal disclaimer.

(21) Appl. No.: 12/823,665

(22) Filed: Jun. 25, 2010

(65) Prior Publication Data

US 2011/0027823 A1 Feb. 3, 2011

Related U.S. Application Data

(60) Provisional application No. 61/269,588, filed on Jun. 27, 2009.

(51) Int. Cl.
*C12Q 1/14* (2006.01)
(52) U.S. Cl.
USPC .......................................................... 435/36
(58) Field of Classification Search
USPC .......................................................... 435/36
See application file for complete search history.

(56) References Cited

U.S. PATENT DOCUMENTS

| 4,035,238 | A | 7/1977 | Meyer et al. | |
|---|---|---|---|---|
| 6,022,682 | A | 2/2000 | Mach et al. | |
| 6,548,268 | B1 | 4/2003 | Rambach | |
| 7,087,401 | B2 | 8/2006 | Sandberg et al. | |
| 7,335,485 | B2 | 2/2008 | Black et al. | |
| 8,268,579 | B2* | 9/2012 | Edberg | 435/34 |
| 8,268,580 | B2* | 9/2012 | Edberg | 435/34 |
| 8,420,347 | B2* | 4/2013 | Edberg | 435/36 |
| 2005/0124026 | A1 | 6/2005 | Walsh et al. | |
| 2006/0019330 | A1 | 1/2006 | Lakshmi et al. | |
| 2009/0191577 | A1* | 7/2009 | Edberg | 435/13 |
| 2011/0151495 | A1* | 6/2011 | Edberg | 435/24 |
| 2011/0269160 | A1* | 11/2011 | Edberg | 435/13 |
| 2011/0269163 | A1* | 11/2011 | Edberg | 435/23 |

FOREIGN PATENT DOCUMENTS

| WO | 9855644 | 12/1998 |
|---|---|---|
| WO | 9950438 | 10/1999 |
| WO | 0053799 | 9/2000 |

OTHER PUBLICATIONS

Yazdankhah et al. "Simple and Direct Detection of *Staphylococcus aureus* in Milk by a Tube Coagulase Test", Letters in Applied Microbiologu, vol. 27, No. 2, Aug. 1998, pp. 111-115.
Selepak et al. "Inoculum Size and Lot-to-Lot Variation as Significant Variables in the Tube Coagulase Test for *Staphylococcus-aureus*", Journal of Clinical Microbiology, vol. 22, No. 5, 1985, pp. 835-837.

Boothby et al. "Tandem Coagulase Thermo Nuclease Agar Method for the Detection of *Staphylococcus-aureus*", vol. 37, No. 2, 1979, pp. 298-302.
Chang et al. "Evaluation of a Latex Agglutination Test for Rapid Identification of *Staphylococcus aureus* from Foods", vol. 56, No. 9, 1993, pp. 759-762.
Perry et al. "Evaluation of *S. auereus* ID, a New Chromogenic Agar Medium for Detection of *Staphylococcus aureus*", Journal of Clinical Microbiology, vol. 41, No. 12, Dec. 2003, p. 5695-5698.
Clancy, "Active Screening in High-Risk Units Is an Effective and Cost-Avoidant Method to Reduce the Rate of Methicillin-Resistant *Staphylococcus aureus* Infection in the Hospital", Infection Control and Hospital Epidemiology, Oct. 2006, vol. 27, No. 10, p. 1009-1017.
Baird et al. 'Media used in the Detection and Enumeration of *Staphylococcus*', International Journal of Food Microbiology, 1995, vol. 26, p. 209-211.
Perry et al., 'Development and Evaluation of a Chromogenic Agar Medium for methicillin-resistant *Staphylococcus aureus*', Journal of Clinical Microbiology, 2004, vol. 42, p. 4519-4523.
Stevens et al., "Use of trehalose-mannitol-phosphatase agar to differentiate *Staphylococcus epidermidis* and *Staphylococcus saprophyticus* from other coagulase-negative *staphylococci*", Journal of Clinical Microbiology, 1984, vol. 20, p. 977-980.
Jordens et al., J. Med. Microbiol., 1989, vol. 30, p. 245-252.
Freydiere et al., "Staphychrom 2, a new specific staphylocoagulase test using a chromogenic substrate", Clinical Microbiology and Infection, 2002, vol. 8, Supplement 1, p. 392.
Loulergue et al., "Evaluation of a new chromogenic medium for isolation and presumptive identification of methicillin resistant *Staphylococcus aureus* from human clinical specimens", Eur. J. Clin. Microbiol. Infect. Dis., 2006, 25(6), p. 407-409.
Bayliss et al., "Plasma coagulation by microorganisms other than *Staphylococcus aureys*", Journal of Bacteriology, 1965, vol. 89, No. 1, p. 101-105.
Lominski et al. "An Improved Direct Coagulase Test for the Rapid Detection of *Staphylococcus Aureus*", British Medical Journal 1948, vol. 116, No. 4546, p. 343.
Varettas et al. "Anticoagulant Carryover May Influence Clot Formation in Direct Tube Coagulase Tests from Blood Cultures," Journal of Clinical Microbiology, vol. 43, No. 9, Sep. 2005, pp. 4613-4615.

(Continued)

Primary Examiner — Ralph Gitomer

(57) ABSTRACT

A presence/absence test for *Staphylococcus aureus* (*S. aureus*) involves placing a first generation test sample in a solution that will clot in the presence of *S. aureus*. The solution contains components that will selectively grow *S. aureus* and also contains clotting factors that will react with *S. aureus*, if *S. aureus* is present in the sample, to clot the solution. Examples of specimen samples that can be tested include nasal swabs and lesion swabs, among others. The test can also be modified to detect the presence or absence of methicillin resistant *S. Aureus* (MRSA). The addition of micro particles having a size in the range of about 0.1 micron to about 1.0 mm provides localities where the bacteria agglomerate, thereby significantly decreasing the clotting time, and providing a significantly stronger clot. The micro particles can be used in other bacteria tests to accelerate the production of an end result. Such other tests can include a vancomycin-resistant *enterococcus* test; a Group B *Streptococcus* test; a test for hemolytic *E. coli*; and a test for *Listeria monocytogenes*, to name a few. These tests are all performed in a liquid broth-type reagent mixture and do not necessarily involve clotting of the broth.

13 Claims, 1 Drawing Sheet

(56) References Cited

OTHER PUBLICATIONS

Carret et al. "Relative Value of Staphlyo Coagulase and Fibrinogen Affinity for the Identification of *Staphylococcus-Aureus*", Journal of Applied Bacteriology, vol. 53, No. 3, 1982, pp. 351-354.

Carey et al. "The Combined Oxacillin Resistance of Coagulase (CORC) Test for Rapid Identification and Prediction of Oxacillin Resistance in *Staphylococcus* Species Directly from Blood Culture", Journal of Clinical Pathology, vol. 61, No. 7, Jul. 1, 2008, pp. 866-868.

Bottone et al. "Rapid Detection and Identification of Methicillin-Resistant *Staphylococcus Aureus* Directly from Positive Blood Cultures Exhibiting Gram-Positive Cocci in Clusters", Clinical Microbiology ewsletter, vol. 29, No. 18, Aug. 31, 2007, pp. 137-139.

Smyth et al. "Mannitol Salt Agar-Cefoxitin Combination as a Screening Medium for Methicillin-Resistant *Staphylococcus Aureus*", Journal of Clinical Microbiology, Aug. 2005, vol. 43, No. 8, pp. 3797-3799.

McDonald et al. "Rapid Identification of *Staphylococcus aureus* from Blood Culture Bottles by a Classic 2-Hour Tube Coagulase Test", Journal of Clinical Microbiology, Jan. 1995, p. 50-52.

Goldstein et al. "Microtube Coagulase Test for Detection of Coagulase-Positive *Staphylococci*", Journal of Clinical Microbiology, May 1982, p. 848-851.

Hauschild et al. "A Modified Pork Plasma Agar for the Enumeration of *Staphylococcus aureus* in foods", Canadian Journal of Microbiology, vol. 25, Jun. 4, 1979, p. 1052-1057.

Lindberg et al. "High Rate of Transfer of *Staphylococcus aureus* from Parental Skin to Infant Gut Flora", Journal of Clinical Microbiology, vol. 42, No. 2, Feb. 2004, p. 530-534.

Bascomb, S., et al. "Use of Enzyme Tests in Characterization and Identification of Aerobic and Facultatively Anaerobic Gram-Positive Cocci", Journal of Clinical Microbiology Reviews, vol. 11, No. 2, Apr. 1988, p. 318-340.

GP Product Information, "VITEK 2 Systems Product Information", the Vitek® 2 Gram-Positive identification card, 069042-4EN1, p. 2-1 through 2-23.

Kloos, W.E., et al. Journal of Clinical Microbiology, "Identification of *Staphylococcus* Species with the API STAPH-IDENT System", vol. 16, No. 3, Sep. 1982, p. 509-516.

Remel, Inc., "RapID™ STAPH PLUS System", IFU 831 1009, Rev. Jan. 4, 2007, p. 2-6.

Rambach, A., BD Diagnostics, BBL CHROMagar, "A Lean Approach to Testing", Feb. 2007, p. 2-14.

Lindsey, J.A., et al. "Indentification of *Staphylococcus epidermidis* and *Staphyloccus hominis* from Blood Cultures by Testing Susceptibility to Desferrioxamine", European Journal of Microbiology & Infectious Diseases, 12:127-131 (1993).

\* cited by examiner

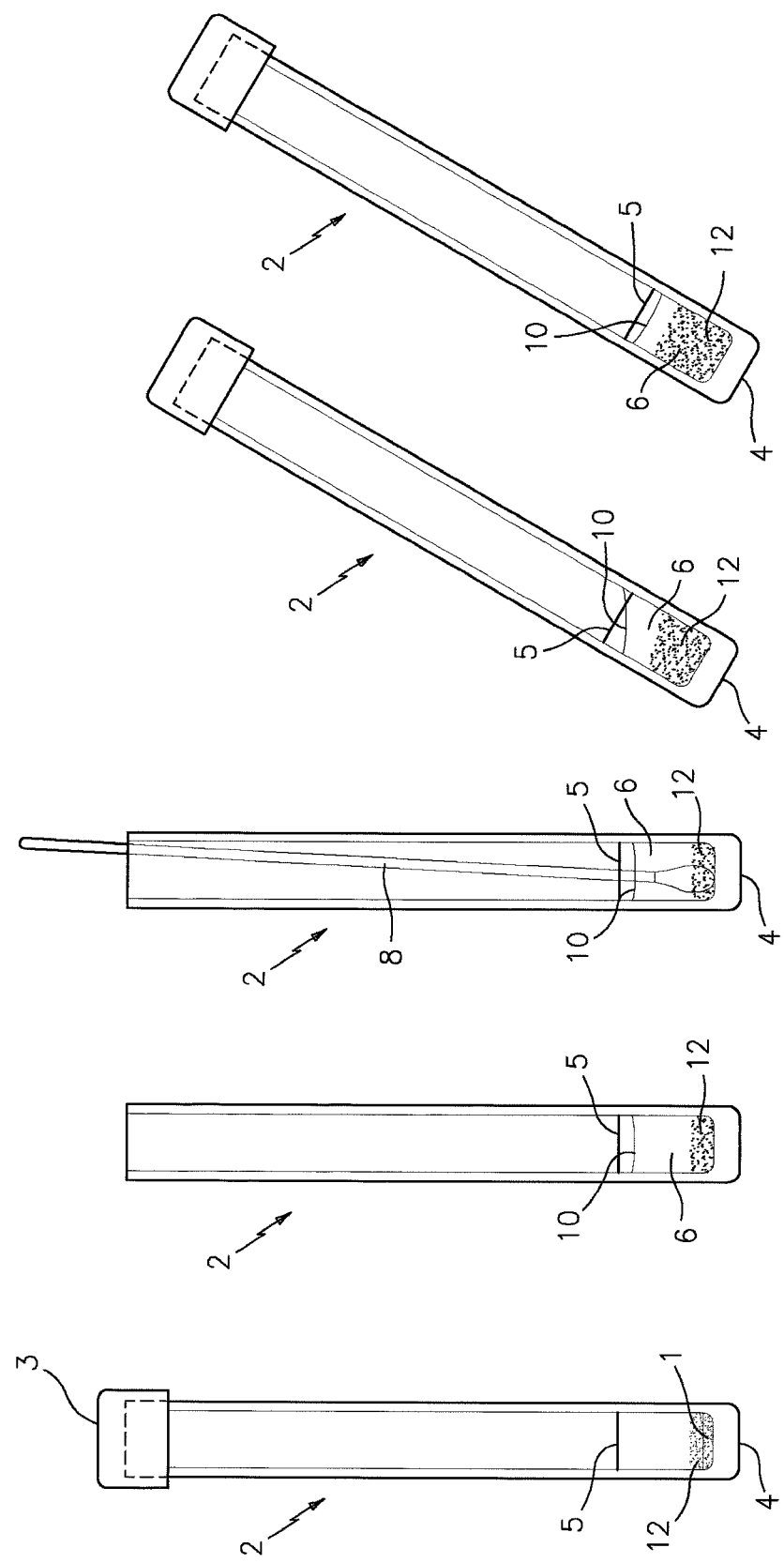

METHOD FOR DETECTING THE PRESENCE OR ABSENCE OF PATHOGENIC STAPHYLOCOCCI IN A TEST SAMPLE, INCLUDING TEST MIXTURE WITH MICRO PARTICLES

This application claims benefit of Provisional application 61/269,588 filed Jun. 27, 2009.

BACKGROUND OF THE INVENTION

1. Technical Information

The present method and test mixture relates to the detection of *Staphylococcus aureus* in a biological, environmental, or food sample, and more particularly to those methods and test mixtures utilizing reacting factors which the target microbe(s) can convert into a clot. Microscopic particles are added to the testing medium to accelerate the formation of microbial biofilms and thus accerate the detection procedure. Preferred particles are microscopic glass beads, but they could be made of some other material. The particles should have a diameter size of from 0.1 micron to 1.0 mm. Generally, they can be classified as micro particles.

2. Background Information

*Staphylococcus aureus* ("*S. aureus*") can be a virulent pathogen of animals and humans. Moreover, it can cause severe food poisoning by the production of a toxin. Diseases caused by *S. aureus* cover a very wide clinical spectrum, from simple skin infections to life threatening infections of the bones, heart, and organs. Of particular concern is the recognition that *S. aureus* infection is common after surgery. It is also associated with intravenous tubing and other implants.

The bacterium *S. aureus* may be transmitted between healthy individuals by skin to skin contact, or from a commonly shared item or a surface (e.g., tanning beds, gym equipment, food handling equipment, etc.) where the transfer may be made to a subsequent person who uses the shared item or touches the surface. Of great medical concern is the recognition that healthy people entering hospitals may "carry" *S. aureus* (e.g., on their skin, or in their noses, etc.) without any signs or symptoms that they do so. In the presence of favorable conditions (often found in but not limited to hospitals), the *S. aureus* can activate and cause serious infection. In addition, *S. aureus* can also be a source of food poisoning, often caused by a food handler contaminating the food product (e.g., meat, poultry, eggs, salads containing mayonnaise, bakery products, dairy products, etc.).

There are two categories of *S. aureus* based on an individual clone's susceptibility to the class of antibiotics that began with methicillin. These are methicillin susceptible *S. aureus* (MSSA), and methicillin resistant *S. aureus* (MRSA). Until only a few years ago, MRSA was most commonly found in hospitals. Now, many are also present in the noses, skin, etc. of people in the non-hospital community. Moreover, these MRSA are increasingly causing serious infections in the community. MRSA is particularly serious because very few antibiotics (e.g., vancomycin) have been shown to be uniformly effective against MRSA.

The Center for Disease Control and Prevention actively surveys for the development of methicillin resistant *S. aureus*. In 2000, the Society for Healthcare Epidemiology of America guidelines recommended contact isolation for patients with MRSA. In addition to the morbidity and mortality caused by MRSA, it has been estimated that each case of infection costs at least $23,000. Accordingly, many hospitals and nursing homes proactively sample patients for MRSA [Clany, M., Active Screening in High-Risk units is an effective and cost-avoidant method to reduce the rate of methicillin-resistant *Staphylococcus aureus* infection in the hospital, Infection Control and Hospital Epidemiology 27:1009-1017, 2006].

Meyer et al. (U.S. Pat. No. 4,035,238) describes the use of a broth for the detection of *S. aureus* that utilized mannitol as a source of carbon and DNA methyl green as an indicator. Neither of these chemicals are coagulase reactive substrates.

Rambach (U.S. Pat. No. 6,548,268) employs at least two chromogenic agents in an agar medium: 5-bromo-6-chloro-indoxyl-phosphate; and 5-bromo-4-chloro-3-indoxyl glucose in the presence of deferoxamine. An individual colony hydrolyzing these substrates will produce colors that will mix with each other and not be independent of one another.

A large number of classical culturing procedures are utilized to detect MSSA and MRSA from human, animal, food, etc. samples. They have in common a basic medium with chemical inhibitors such as 6-8% sodium chloride, potassium tetlurlte, and a variety of antibiotics. For example Stevens and Jones described the use of a trehalose-mannitol-phosphatase agar [Stevens, D L and Jones, C. Use of trehalose-mannitol-phosphatase agar to differentiate *Staphylococcus epidermidis* and *Staphylococcus saprophyticus* from other coagulase-negative *staphylococci*, J. of Clin. Microbiology 20:977-980, 1984]. The use of mannitol as a carbon source and salt as a selective agent into an agar known as mannitol-salt agar has been commonly used in clinical laboratories [Baird, R. M. and W. H. Lee., Media used in the detection and enumeration of *Staphylococcus aureus*, Int. J. Food Microbiology. 26:209-211, 1995]. Within the prior art of culturing, it is generally accepted procedure to perform coagulase tests utilizing samples of *S. aureus* that are isolated in a pure culture.

The procedure "*S. aureus* ID" [Bio Merieux, La Balme Les Grottes, France] uses an alpha-glucosidase substrate in agar to detect *S. aureus*. A single substrate is utilized. [Perry, J. D. et al., Evaluation of *S. aureus* ID, a new chromogenic agar medium for detection of *Staphylococcus aureus*, J. Clin. Microbiology 41: 5695-5698, 2003]. A variant of this medium, which contains added antibiotics and sodium chloride, is designed to detect MRSA [Perry et al., Development and evaluation of a chromogenic agar medium for methicillin-resistant *Staphylococcus aureus*, J. of Clin. Micro. 42:4519-4523, 2004].

Selepak and Witebsky disclose a study evaluating the inoculum size and lot-to-lot variability of the tube coagulase test for *S. aureus*. Specimens were collected and isolates were generated from the bacterial colonies on agar plates. Tubes containing anticoagulated rabbit coagulase plasma were inoculated with a part of, or more than one, staphylococcal colony from the isolates. The tubes were incubated and examined for the presence of clot. According to Selepak and Witebsky, with some isolates and some lots of coagulase plasma, even a single colony [from the isolate] may not provide enough inoculum for a positive coagulase test. Selepak and Witebsky state that: "Expressed more quantitatively, at least 8 log 10 organisms per ml should be used whenever possible for each coagulase tube test. Our data further suggest that *S. aureus* does not grow in coagulase plasma; therefore, the incubation of coagulase plasma for 18 to 24H does not compensate for the use of small inoculum." Thus, Selepak and Witebsky indicate that it is impractical, if not impossible, to detect the presence or absence of *S. aureus* in first generation biological specimen samples using a direct coagulase test. [Selepak, S. T. et ai, "Inoculum Size and Lot-to-Lot Variation as Significant Variables in the Tube Coagulase Test for *Staphylococcus aureus*", Journal of Clin. Microbiology, November 1985, p. 835-837].

It would, therefore, be desirable to provide a test mixture and a method that can rapidly detect *S. aureus* directly from a sample, one that does not require a skilled technician to perform the method, one that can be performed without the need to develop isolates from the specimen (i.e., one that can be performed on a first generational sample), and one that does not require a large concentration of *S. aureus* organisms to be accurate.

SUMMARY OF THE INVENTION

This invention relates to a method and test mixture for specific detection of *S. aureus* bacteria in a biological, environmental, or food specimen. In the detection of *S. aureus*, a test mixture (which mixture may also be referred to as a "medium") is utilized that includes coagulase substrates (sometimes referred to as "coagulase reacting factors") that react specifically with coagulase produced by *S. aureus* to form a clot, admixed with constituents that facilitate the multiplication of *S. aureus* (also referred to as "growth promoting constituents"). Hence, the present method and test mixture utilize coagulase substrates that are activated by the coagulase produced by *S. aureus*, and the enzyme coagulase is specific to pathogenic *staphylococci*, as is disclosed in the Code of The Federal Register, Title 21, Chapter 1, Sub Part C, Sec. 866.2160 "Coagulase Plasma". Inhibitors and antibiotics may be included to inhibit or otherwise negatively affect competing bacterial growth, but are not required. The untreated sample (e.g., collected from a nasal swab from a person, or off of a surface, etc.) is added to the test mixture, and the inoculated test sample is incubated. If *S. aureus* is present within the sample, the *S. aureus* will multiply within the test mixture and will produce coagulase that reacts with the coagulase substrates. The reaction between the coagulase produced by the *S. aureus* and the coagulase substrates within the test mixture will produce a detectable clot within the test mixture in a time period typically between two and twenty-four hours, positively indicating the presence of *S. aureus*.

Under the present method, the clot may be dissolved to release viable *S. aureus* into a liquid, which liquid can then be subjected to further analyses, including but not limited to: antibiotic susceptibility tests, molecular fingerprinting, genetic analysis, etc. As will be described below in greater detail, the antibiotic cefoxitin or an inducer of the mecA gene may be included within the test mixture to enable methicillin resistant *S. aureus* (MRSA) specific testing within the first generational sample, or the dissolved clot mixture may be tested to ascertain the presence or absence of MRSA therein.

The test mixture is preferably prepared in a form that facilitates handling, packaging, storing, etc., of the test mixture. A dry powder that can be hydrated into liquid form is a particularly preferable form for the test mixture, but the present invention is not limited to a powder form. The test mixture may assume a liquid form, or any other form (e.g., paste, gel, etc.), preferably one that can be hydrated for use. The dry powder will also contain the micro particles referred to above.

The coagulase substrates within the test mixture may be provided within plasma, or may be provided by another substance that is operative to react with the coagulase produced by *S. aureus* to form a clot. Present testing indicates that rabbit plasma is a favorable source of a coagulase substrate. Other plasmas (e.g., pork plasma) may be used alternatively. Fibrinogen is another example of a source of a coagulase substrate. In those embodiments that utilize plasma as a source of a coagulase substrate, it may be preferable to add a non-plasma source of a coagulase substrate to the test mixture to ensure an adequate source of coagulase substrate within the test mixture. As an example, our testing indicates that combining fibrinogen and rabbit plasma within the test mixture is an effective means for ensuring a consistent, adequate source of coagulase substrates. An advantage of adding a material such as fibrinogen to the test mixture is that it increases the performance consistency of the test mixture, and makes the method less susceptible to variability that may occur with plasma.

The growth promoting constituents within the test mixture that facilitate the multiplication of and sustain *S. aureus* can be varied to suit the application. Those in the art will recognize that many different combinations of constituents, and varying relative amounts of the same constituents, can be used to provide the same functionality Growth promoting constituents include sources of nitrates and proteins, material operative to assist in the generation of nucleic acid synthesis, sources of energy for the *S. aureus*, sources of amino acid growth factor, and in some embodiments materials operable to help repair damaged target organisms. This list of growth promoting constituents does not represent all of the materials that can be beneficial within the test mixture, but does illustrate materials that are acceptable (e.g., vitamins, salts, minerals, inorganic moieties, etc.). The test mixture may include other constituents that benefit the performance of the test mixture.

In most applications of the present invention, it will be desirable to utilize a test mixture that includes the following: a) an effective amount of amino acids; b) an effective amount of nitrogen sources; c) an effective amount of salts; d) an effective amount of vitamins; and e) an effective amount of calcium. Those skilled in the art will recognize that natural sources of such amino acids can be used rather than pure sources. The natural sources (e.g. extract of whole organisms, such as yeast) may be in mixture form or in purified form. The natural mixtures can contain varying amounts of such amino acids and vitamins. Those skilled in the art will further recognize that many different combinations of amino acids and vitamins can be used in present invention test mixture. The medium also includes a plurality of micro particles preferably from about 0.1 micron to about 1.0 mm in diameter.

Those in the art will further recognize that carbon, nitrogen, trace elements, vitamins, amino acids and selective agents can be provided in many forms. Generally, it is preferred to have an amount of vitamins and amino acids within a predetermined range, but those in the art will recognize that the actual properties of each ingredient may be varied so that reduction in the amount of one ingredient can be compensated by an increase in the amount of another. This is particularly relevant when the essential amino acids, trace elements or vitamins of the microbes sought to be detected are known. Some ingredients may be provided in reduced amounts or deleted if they may be synthesized endogenously by the microorganism whose presence is to be determined. Salts may be provided as a source of ions upon dissociation.

The test mixture may be packaged in a container (e.g., a test tube, a container with a flat bottom wall, etc.) that facilitates the testing process. If the medium is prepared in a form that can be hydrated, the mixture can be hydrated with sterile water or non-sterile water.

To detect the presence of MSSA or MRSA within a sample, the sample is obtained from a biological, environmental, or food specimen. A sample collected using a nasal swab is an example of a first generation sample that is particularly convenient to collect and test using the present invention. Once collected, the sample is inoculated into the test mixture.

The inoculated sample is incubated under conditions favorable to facilitate the multiplication of any S. aureus that may be present within the inoculated sample. In the case of a powdered test mixture hydrated with water, the incubation may be carried out at temperatures between about 200° C. to 42° C. The combination of sequential enzyme specificity, S. aureus enhancing growth factors, and antibiotic selectivity provides multiple hurdles which prevent the competing non-target bacteria from being detected within the test period; e.g. 24 hours or less.

The present invention test and method can be used in hospital admissions, routinely in intensive care units, in nursing homes, dialysis patients, people receiving home immunosuppressive therapy, and the like. It can also be used in environmental settings (e.g., gyms, tanning salons, restaurants, etc.) where the bacteria S. aureus may be transferred from a human carrier and it can be used to test various different foods for S. aureus contamination. It will be appreciated that a substantial benefit of the present method and mixture is that they may be performed/used without the need for expensive equipment or skilled medical technologists. Another substantial benefit of the present method/mixture is that it is operable with a relatively small amount of S. aureus within the test sample; e.g., the present method/mixture has detected S. aureus in samples having concentrations of S. aureus as low as 100 CFU/ml.

BRIEF DESCRIPTION OF THE DRAWINGS

Details of the invention will become more readily apparent from the following detailed description of several embodiments of the invention when taken in conjunction with the accompanying drawings in which:

FIG. 1 is a side elevational view of a test tube containing a powder culturing mixture which is formulated to detect the presence or absence of S. aureus in a first generation biological sample of a nasal swab;

FIG. 2 is a side elevational view of the test tube of FIG. 1, but showing the culturing mixture having been hydrated by water;

FIG. 3 is a side elevational view of the test tube FIG. 2 and showing a cotton swab inserted into the test tube to deposit a first generation biological specimen nasal swab in the medium;

FIG. 4 is a side elevational view of the test tube of FIG. 3 after the specimen has been deposited and cultured in the medium for a period of time and indicating the absence of S. aureus in the specimen; and FIG. 5 is a side elevational view similar to FIG. 4 but showing the test tube medium after the culturing period and indicating the presence of S. aureus in the specimen.

DETAILED DESCRIPTION OF THE INVENTION

FIG. 1 is a side elevational view of a test tube denoted by the numeral 2 which preferably has a flat bottom 4 and a top closure 3, and which contains a dry powdered test mixture 1 which is formed in accordance with this invention for detecting the presence or absence of S. aureus in a sample; e.g., a first generational biological sample. The tube 2 is also provided with a reference line 5 which indicates the amount of water to be added to the tube 2 in order to properly hydrate the powdered mixture 1 for specimen sample testing. The drawings show the micro particles referred to above as numeral 12 in the sampling tube.

Acceptable hydrated test mixtures can be made using the following constituents in the ranges indicated, to create 15 ml of test mixture:

| Constituent | Quantity per 15 ml of Test Mixture | Range per 15 ml of Test Mixture |
| --- | --- | --- |
| Nitrate Broth | 7.5 ml | 1.0 ml-9.0 ml |
| Water | 7.5 ml | 1.0 ml-9.0 ml |
| Uracil | 10.0 mg | 1.0 mg-20.0 mg |
| Sodium Pyruvate | 10.0 mg | 1.0 mg-20.0 mg |
| L-glutamine | 20.0 mg | 5.0 mg-40.0 mg |
| Sodium Sulfite | 1.0 mg | 0.5 mg-2.0 mg |
| Rabbit Plasma | 100.0 mg | 15.0 mg-500.0 mg |
| Fibrinogen | 100.0 mg | 15.0 mg-500.0 mg |
| Micro Particles | 25.0 mg | 1.0 mg-50.0 mg |

The specific example of the constituent quantities per 15 ml of test mixture provided above represents a particular test mixture formulation that was tested and found to perform satisfactorily. The micro particles are preferably uncoated glass beads with a diameter in the range of about 0.01-5.0 mm. This specific example does not represent all test mixture formulations, and the present invention is not limited thereto. As stated above, those in the art will recognize that many different combinations of constituents, and varying relative amounts of the same, can be used to provide the same functionality. Hence, the present methods and mixture contemplates that a number of different constituent formulations can be made within the aforesaid ranges.

As noted in FIG. 2, the powdered mixture 1 is properly hydrated by the addition of water, preferably distilled water, to form a hydrated test mixture 6 into which the sample (e.g., carried on a nasal swab) is deposited.

First generational test samples can be collected by a variety of different techniques; e.g., a human sample can be collected by wiping a swab within the nose of a subject. Nasal swabs are a particularly convenient way of collecting a test sample, but they are not the only collection method; e.g., test samples can be collected from throat swabs, skin lesions, undamaged skin, etc. First generational environmental samples can be collected by various known methods; e.g., wiping or swabbing a surface using a dry or wet wipe/swab. Likewise, first generational food samples can be collected form the food itself, or wiping food residue from surfaces in contact with the food, etc. Once the sample is collected, it can be deposited in the hydrated test mixture 6; e.g., using the same cotton swab 8 which has been used to gather the first generation sample from the source thereof. Once the specimen sample is deposited in the test mixture 6, it is incubated within the test mixture for a period of time typically less than twenty-four hours. The incubation may occur at any temperature that is acceptable under the circumstances. After the inoculation period, the container (e.g., test tube 2) holding the inoculated test mixture can be inspected for the presence of a clot; e.g., the test tube 2 can be tilted to one side as shown in FIGS. 4 and 5 to see if the meniscus 10 of the test mixture will move or whether a clot keeps the test mixture below a reference line 5. The presence of a clot indicates that S. aureus is present in the test sample, and the absence of a clot in the inoculated test mixture indicates that S. aureus is not present in the test mixture 6, as shown in FIG. 4. In some instances, the entire inoculated test mixture will clot, and in others some liquid will remain in the container with the clot. Approximately 80% of the present tests performed using first generation nasal samples clotted within six hours when S. aureus is present in the first generation test sample.

To determine the effectiveness of the present method and mixture, a control study was performed involving sixty (60) control samples titred to contain varying amounts of MSSA, and sixty (60) control samples containing varying amounts of MRSA Standard clones of MSSA and MRSA were grown in trypticase soy broth (TSB), and were diluted by log 10 increments. The present invention test mixture was inoculated with a set amount (0.1 ml) of each the control samples. A first set of the inoculated test mixtures were incubated at 35° C., and second set of the inoculated test mixtures were incubated at 23° C. Of the sixty control test samples, all were positive for S. aureus in five hours, forty-nine (49) were positive in four hours; thirty-six (36) were positive in three hours, and twenty-four (24) in two hours. Data detailing the relationship between the concentration of the inoculum, and incubation temperature was as follows:

| S. aureus CFU/ml | Clot at 35° C. | Clot at 23° C. |
| --- | --- | --- |
| 7 log 10 | 2.0 hr | 3.0 hr |
| 6 log 10 | 3.0 hr | 3.0 hr |
| 5 log 10 | 4.0 hr | 4.0 hr |
| 4 log 10 | 6.0 hr | 7.0 hr |
| 3 log 10 | 10.0 hr | 11.5 hr |
| 2 log 10 | 15.0 hr | 21.0 hr |

The concentration of S. aureus within the clots were all at least 5 log 10.

In addition to the above described control study, a clinical study was performed using fifty samples. The samples were taken from a medical intensive care unit by culturing patient nares. The patients were not identified, nor were the results of any standard culture available (FDA protocol). The samples were plated on mannitol salt agar (MSA) using swabs. After plating the samples on MSA, the swabs were used to inoculate the test mixture. Clotting was observed for each hour for twenty-four hours. There were no false positives.

| Bacteria | Number of Samples Detected Positive for Identified Bacteria by Both MSA Method and Present Method | Number of Samples Detected Positive for Identified Bacteria by Present Method Alone | Number of Samples Detected Positive for Method Identified Bacteria by MSA Alone |
| --- | --- | --- | --- |
| MSSA | 9 | 2 | — |
| MRSA | 13 | 2 | 1 |

When a clot was observed, a portion of the clot was removed and dissolved. A quantitative count of CFU/ml was performed from the dissolved clot material.

In some embodiments, the present method/mixture may include means to distinguish between MSSA and MRSA. For example, cefoxitin in a concentration of about 10-100 mg/ml or another MecA gene inhibitor can be included in the test mixture. Any MSSA present within the test sample will be killed, but MRSA will not. Thus, if a clot does form, the S. aureus in the test sample will have been shown to be MRSA. If a clot forms and conforms the presence of MRSA, the clot can then be dissolved in order to perform further analyses of the S. aureus bacterium detected. In some embodiments, a metabolizable substrate or substrates may be included to enhance the specificity of the test. These may include a hydrolyzable substrate, sugar, or amino acids. When metabolized by the target microbe, a sensible signal is produced that provides an additional indication that the target microbe is present, thus enhancing specificity.

It will be appreciated that the test of this invention is significantly simpler to perform than the standard tests which are currently in use, as typified by the coagulase plasma procedure suggested by Remel Products, Thermo Fisher Scientific, Lenexa, Kans., U.S.A. The Remel procedure, which is approved by the FDA and appears in the Code of the Federal Register as an exempt test, requires a two step test for S. aureus wherein microbe colonies from the specimen are first grown in an agar medium and screened for suspected S. aureus colonies using a gram stain and catalase slide test before proceeding to a second coagulase test step. There are complications relating to the Remel type of coagulase test, namely: 1) colonies for coagulase testing must not be picked from media containing high concentrations of salt as false positive results may occur; 2) in the first step slide test procedure, the organism/saline suspension must be observed for auto-agglutination prior to the addition of the coagulase plasma to prevent a false positive test reading; and 3) false negative coagulase reactions may occur if the test culture is older that 18-24 hours, of if there is scant growth.

The addition within the present invention of micro particles having a size in the range of about 0.1 micron to about 1.0 mm provides localities where the bacteria agglomerate, thereby significantly decreasing the clotting time, and providing a significantly stronger clot. The micro particles can be glass, agar, agarose, plastic or some other similar material. The micro particles can be used in other bacteria tests to accelerate the production of an end result. Such other tests can include a vancomycin-resistant *enterococcus* test; a Group *Streptococcus* test; a test for hemolytic *E. coli*; and a test for *Listeria monocytogenes*, to name a few. These tests are all preformed in a liquid broth-type reagent mixture and do not necessarily involve clotting of the broth.

The micro particles increase the surface area in the liquid broth and allow microbes that multiply in vitro to establish a biofilm. In effect, the micro particles act in an analogous way as a catalyst does in a chemical reaction. In the microbiology area, the micro particles provide multiple attachment surfaces for the microbes to "establish residence". Microbes prefer surfaces to grow and multiply on rather than being free is a liquid environment. The microbes experience quorum sensing, which accelerates the generation of a biofilm. The biofilm is produced when the microbes multiply, and it yields colonies of microbes which are held together by external capsules of the microbes which, in the broad context, are surface components, such as polysaccharides, proteins and/or mixtures thereof. The micro particles are inert, and may be colloidal, in suspension, or not in suspension. Any materials or structures that encourage the growth of microbes on a biofilm are highly preferred for use in this invention.

While micro particles are a preferred embodiment of the invention, any structure such as a rod or rods, that increases the surface area inside of the sampling vessel so as to stimulate and accelerate the formation of microbial biofilms that will hasten the growth of the target microbes can be used.

While the invention has been described with respect to specific embodiments, those skilled in the art will readily appreciate that various changes and/or modifications can be made to the invention.

What is claimed is:

1. A method for the detection of the presence or absence of pathogenic *staphylococci* ("*p. staphylococci*") specifically and directly in a first generation test sample, said method comprising the steps of:

providing a hydratable reagent test mixture which comprises reacting factors which *p. staphylococci* can convert into a clot, and an effective amount of micro particles to accelerate the formation of microbial biofilms in a hydrated admixture of the sample and test mixture;

incubating the hydrated admixture of the test sample and test mixture for a time period which is sufficient to form a clot within the admixture if *p. staphylococci* is present in the first generation sample; and detecting the presence or absence of *p. staphylococci* in the sample based on the presence or absence of clotting within the admixture.

2. The method of claim 1 wherein said micro particles have a diameter in the range of about 0.1 micron to about 1.0 mm.

3. The method of claim 2 wherein said micro particles are glass beads.

4. The method of claim 1 further comprising the step of gathering the first generation sample by one of swabbing a nasal passage of a human subject, swabbing an environmental surface, or gathering the first generational sample from a sample of food.

5. The method of claim 1 wherein said test mixture includes a metabolizable substrate that enhances test specificity.

6. The method of claim 1 wherein the test mixture includes an amount of an inducer of the MecA gene, effective to kill methicillin susceptible *S. aureus* ("MSSA") in the test sample.

7. The method of claim 1, wherein the test mixture includes one or more growth promoting constituents that promote the growth of *p. staphylococci* and one or more inhibitors operable to interfere with growth of non-*p. staphylococci* bacteria.

8. The method of claim 1, wherein the test mixture further comprises coagulase substrates operative to react with a coagulase enzyme system produced by *p. staphylococci* in the first generation specimen test sample to create a clot, which coagulase substrates include fibrinogen.

9. The method of claim 8 wherein the test mixture includes plasma as a source of coagulase substrates.

10. The method of claim 9, where the plasma is rabbit plasma.

11. The method of claim 1, wherein the test mixture includes an amount of cefoxitin, effective to kill methicillin susceptible *S. aureus* ("MSSA") in the test sample.

12. The method of claim 1, wherein the test mixture includes a constituent operable to distinguish MRSA from methicillin susceptible *S. aureus* ("MSSA").

13. The method of claim 1, wherein the hydratable reagent test mixture is in the form a dry powder, a liquid, a paste, or a gel.

* * * * *